Figure 1A:
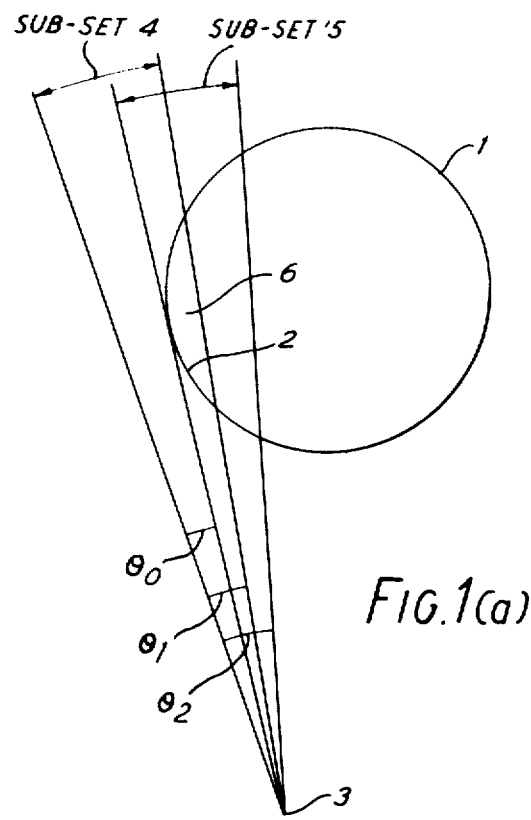

United States Patent [19]

Hounsfield

[11] 4,295,195

[45] Oct. 13, 1981

[54] RADIOGRAPHY

[75] Inventor: Godfrey N. Hounsfield, Newark, England

[73] Assignee: E M I Limited, Hayes, England

[21] Appl. No.: 87,669

[22] Filed: Oct. 24, 1979

[30] Foreign Application Priority Data

Oct. 24, 1978 [GB] United Kingdom ............... 41710/78

[51] Int. Cl.³ ...................... G06F 15/42; G01N 23/00
[52] U.S. Cl. ................................ 364/414; 250/445 T; 364/582
[58] Field of Search .................... 364/414, 575, 582; 250/363 R, 363 S, 445 T, 445 R

[56] References Cited

U.S. PATENT DOCUMENTS

| | | | |
|---|---|---|---|
| 4,032,761 | 6/1977 | Mayo et al. ......................... | 364/414 |
| 4,105,922 | 8/1978 | Lambert et al. ................. | 250/445 T |
| 4,114,040 | 9/1978 | Hounsfield ..................... | 250/445 T |

*Primary Examiner*—Errol A. Krass

*Attorney, Agent, or Firm*—Cooper, Dunham, Clark, Griffin & Moran

[57] ABSTRACT

In a computerized tomographic apparatus of the kind in which the performances of different detectors are normalized causing them to receive radiation along substantially similar paths in various overlap zones within a body under examination, the normalization can be adversely affected by the amount of radiation exposure suffered by each detector prior to its receipt of radiation along the paths in the overlap zones. The invention permits such adverse effects to be reduced or eliminated by averaging the electrical signals, produced by the detectors in respect of the paths in the overlap zones; the signals relating to paths near the center of an overlap zone being combined with the signals relating to other paths distributed substantially across the overlap zone but the signals relating to paths near the edges of an overlap zone being combined with the signals relating to only a few, neighboring paths.

3 Claims, 5 Drawing Figures

RADIOGRAPHY

The present invention relates to radiography, and it relates in particular to a branch of radiography which has become known as computerized tomography (CT).

CT scanners are now an accepted diagnostic tool and they operate by acquiring data relating to the attenuation suffered by penetrative X-radiation on traversing many substantially linear beam paths across a cross-sectional slice of a patient's body, and then processing the data so acquired to produce a representation of the variation of X-ray attenuation or transmission from place to place over the slice.

U.S. Pat. No. 3,778,614 discloses a number of techniques for acquiring the desired data as well as a suitable processing technique.

United States Patent Application Ser. No. 934,311 (now U.S. Pat. No. 4,178,511) describes and claims a CT scanner which is capable of rapid data acquisition and which can produce representations which retain, at least to a substantial extent, the remarkable soft tissue differentiating ability of slower scanners. This new CT scanner is one of a rotate-rotate kind (i.e. the radiation source and an associated array of detectors both execute rotational scanning movements around an axis intersecting substantially normally the body slice under examination). The source of radiation includes an extended radiation-emissive target and means for repetitively deflecting an electron beam to and fro along the anode so as to shift the origin of the radiation accordingly. The relationship between the rotational scanning movements and the repetitive deflection of the electron beam is controlled so that data are acquired in respect of many sets of divergent beam paths disposed at different mean angles in the slice, each set being effectively focussed on, or apparently terminating at, a respective "pivot" point disposed outside the locus followed by the source and detector as they rotate.

Each set is made up of overlapping sub-sets of paths viewed by different detectors, and the paths in the overlap are used, inter alia, for the purpose of evaluating and/or correcting for inter-detector performance differences.

It is usual for the data relating to an overlap zone and derived from one detector to be averaged and compared with the average of the data relating to the same overlap zone and derived from another detector, thereby to normalize the performances of the two detectors. If this is done, however, problems can arise in the event that one detector has received substantially more radiation than the other just prior to its production of data in relation to the overlap zone. This can happen, for example, when an overlap zone occurs adjacent the edge of the body, a bone edge or a substantial volume of air in a patient's lung. The difficulty arises primarily because of the well known phenomenon, in radiation detectors, which is known as "lag". The detector which has been exposed to the greater amount of radiation produces, in relation to the overlap zone, output signals which are contaminated by residual components left over from its prior exposure to the radiation and thus the output signals obtained, in relation to the same zone, from the two detectors, are not compatible. This causes an apparent sharp discontinuity, or so-called "glitch", to occur in the output signals as processed, and can result in the production of artefacts on the finally produced representation.

It is an object of this invention to reduce or eliminate the difficulty referred to above.

According to the invention there is provided a CT scanner having first and second detector devices for producing data indicative of the attenuation suffered by penetrating radiation on traversing respective sub-sets of substantially linear beam paths traversing a cross-sectional slice of a patient's body, said sub-sets overlapping in an overlap zone, means for comparing the average values of the data derived from the overlap zone by the said first and second detector devices and for utilising the result of said comparison to normalise the data provided by the two detectors in relation to the entire sub-sets, and means for operating upon the individual data signals to substantially align the data derived from the two detector devices in relation to the overlap zone, said means for operating including, for beam paths at and adjacent the edge of said zone, means for averaging relatively few output signals from both detectors, comparing the averaged values and normalising the output signals on the basis of said comparison and, for beam paths at and adjacent the centre of the overlap zone, means for averaging substantially all of the signals derived from the overlap zone by the two detector devices, for comparing the averaged signals and effecting normalisation on the basis of the comparison.

Figure 1B:
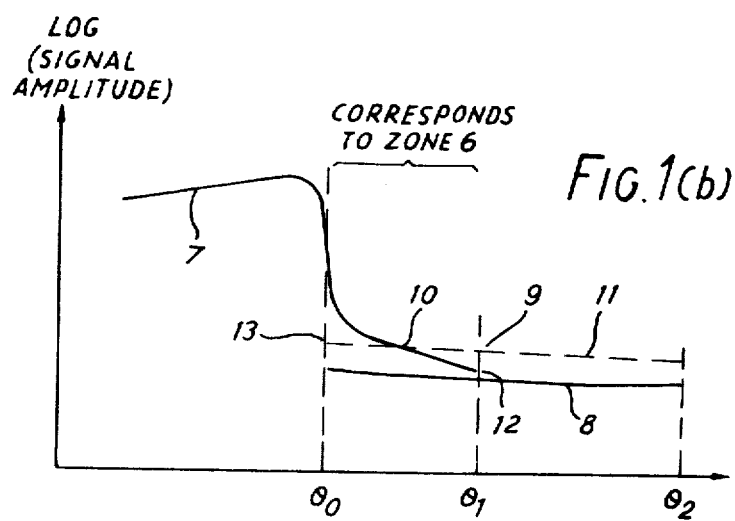
Figure 2:
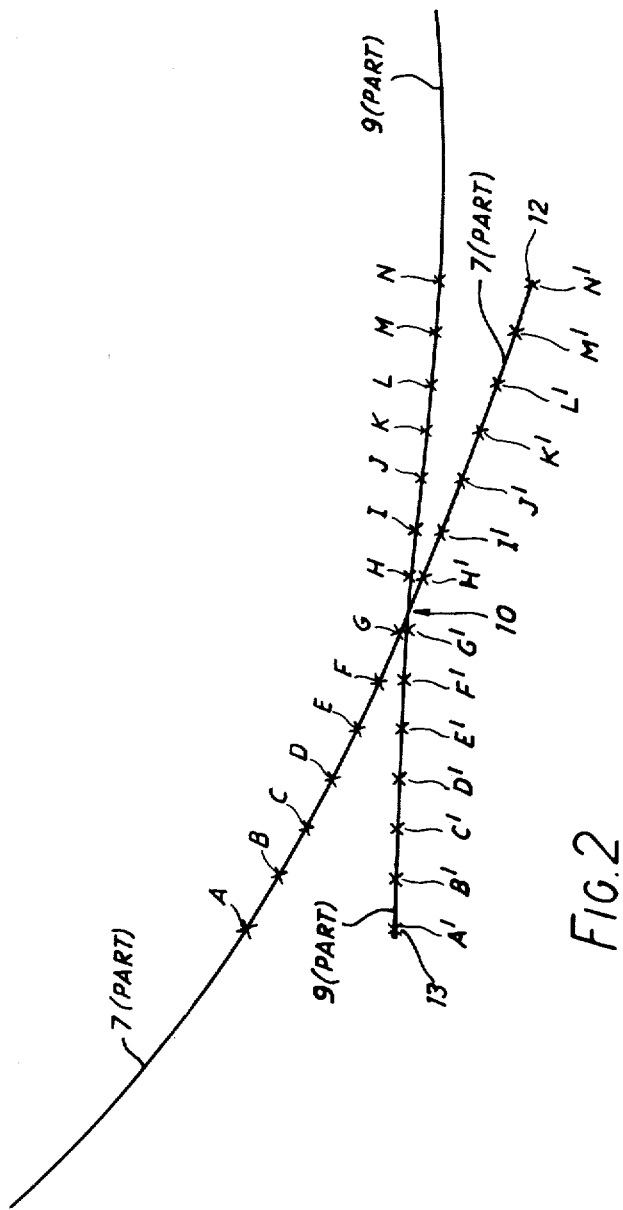
Figure 3:
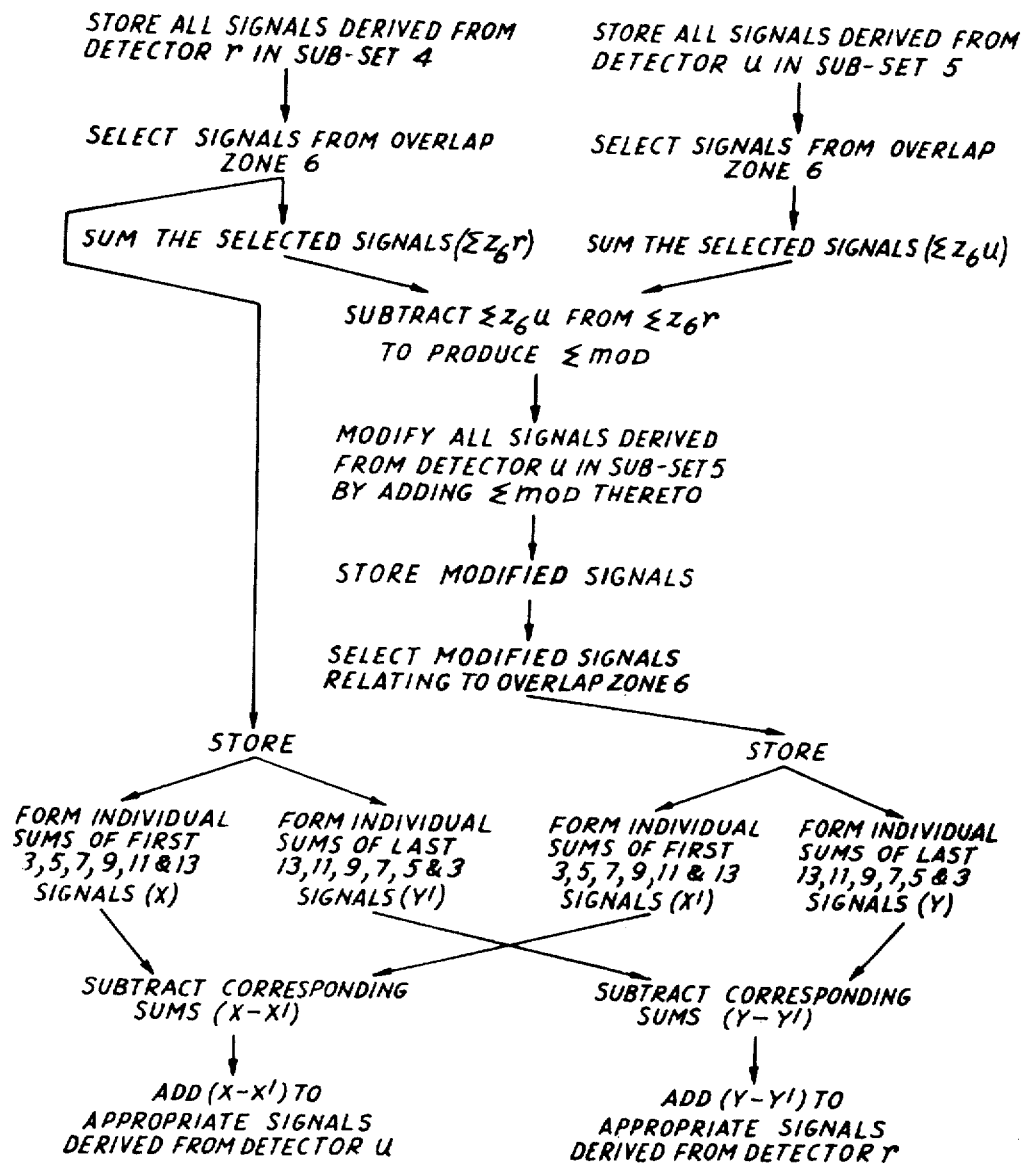
Figure 4:
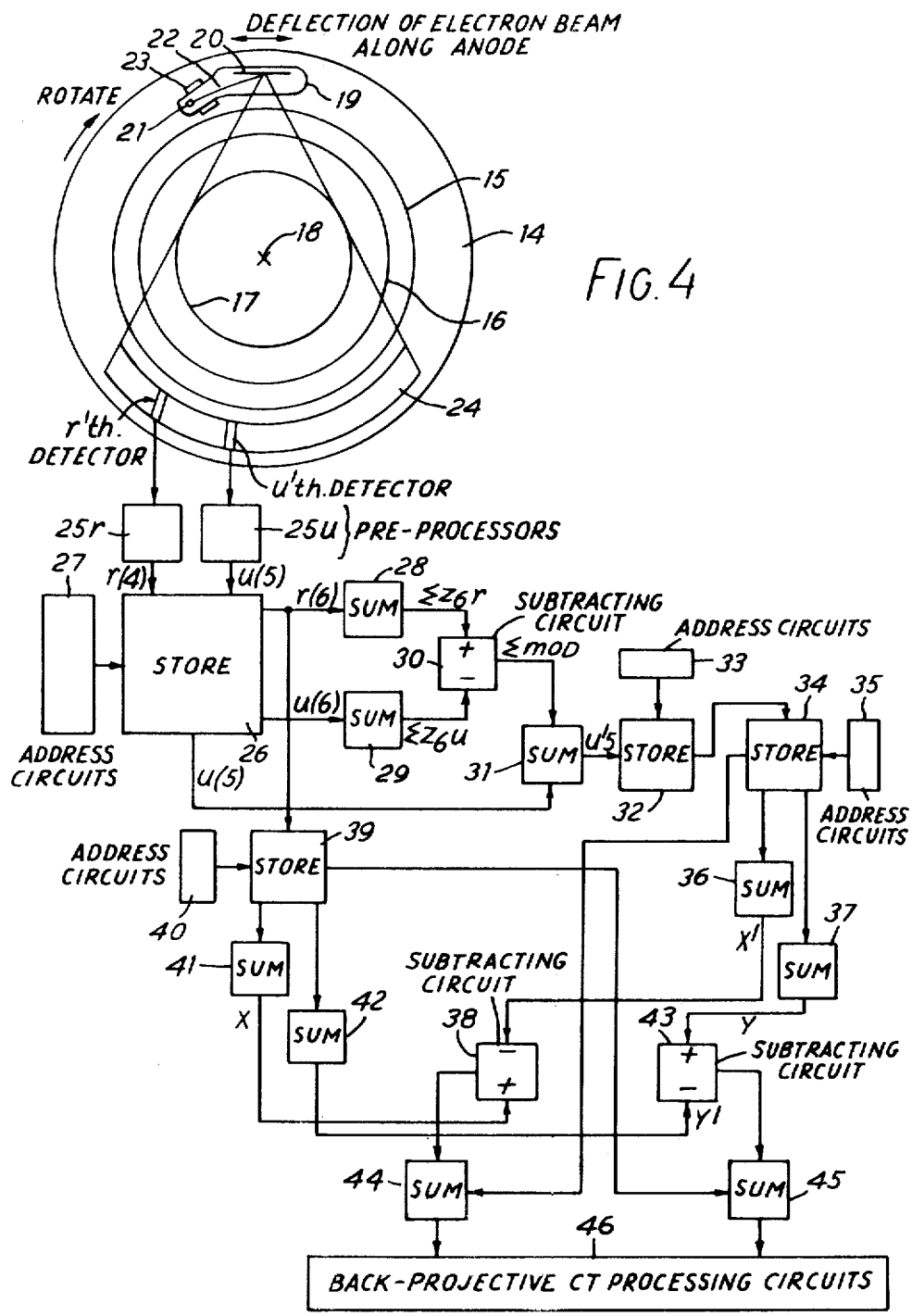

In order that the invention may be clearly understood and readily carried into effect, one embodiment thereof will now be described, by way of example only, with reference to the accompanying drawings, of which:

FIGS. 1(a) and 1(b) show, schematically, how the afore-mentioned "glitch" can arise, FIG. 2 shows, on enlarged scale, the detector output signals of FIG. 1 and is used to assist in explaining how they can be processed, in accordance with one example of the invention, to reduce glitches, FIG. 3 shows a flow diagram of an arrangement for effecting the processing referred to in relation to FIG. 2, and FIG. 4 shows, in block diagrammatic form, a circuit arrangement for effecting the processing referred to in relation to FIG. 2, as well as showing, in schematic form, the elements of a CT scanner.

The disclosure (including the drawings) of United States Patent Application Ser. No. 934,311 (U.S. Pat. No. 4,178,511) is incorporated herein by reference, and it is therefore deemed unnecessary to repeat herein any more of the information contained in that application.

Referring now to FIG. 1, an edge of body 1 under examination by a CT scanner is shown at 2. As has been previously mentioned, a set of divergent beam paths, distributed across the body 1 and focussed upon a common "pivot" point 3 is made up of several overlapping sub-sets, such as 4 and 5, of beam paths viewed by different detectors with an overlap zone such as 6, for each neighbouring pair of sub-sets, in respect of which data are provided by both detectors. In circumstances such as those shown in FIG. 1, the detector which views the paths of subset 4 has been exposed to unattenuated radiation which has passed the edge 2 of the body 1 whereas the detector which views the paths of sub-set 5 has only been exposed to radiation that has been attenuated by the body.

The output signals derived from the first-mentioned detector, therefore, are contaminated by after-glow to a much greater extent than are the output signals derived from the second-mentioned detector. The variation with position across the subset of the output signals (after pre-processing including logarithmic conversion) derived from the two detectors for subsets 4 and 5 are shown schematically at 7 and 8 respectively. It is to be noted that for convenience the curves 7 and 8 are shown inverted from the disposition that they would usually adopt in practice. The means of the output signals derived from both detectors and relating to zone 6 of overlap are formed independently and then subtracted from one another, the difference being added to all of the output signals in line 8. This raises the readings, as shown in dotted line at 9, to intersect the line 7 at a point 10 which is considered, in this example, to coincide with the half-way point of the overlap zone.

It will be appreciated that the complete set of output signals for beam paths converging upon point 3 consists of signals for many sub-sets of paths distributed across the body, the signals for each sub-set being derived from a respective detector and adjacent sub-sets overlapping to produce overlap zones, like zone 6, distributed regularly in angle across the body 1. Each overlap zone can be used to normalize the performances of the two detectors concerned as just described in relation to FIG. 1(b).

It is conventional to use, for processing, the output signals disposed on line 7 as far as the point 10, then the signals disposed on line 9 (i.e. the "corrected" or normalized signals corresponding to line 8) as far as point 11 which corresponds to the centre of the overlap zone between sub-set 5 and the next adjacent sub-set (not shown) towards the centre of the body 1. From point 11, the signals used are those corresponding to the corrected (normalized) signals for the detector viewing the paths of the said next adjacent sub-set, and so on. In this way a chain or normalized signals extending across the body is constructed for the paths converging on pivot point 3. It will be appreciated that the same procedure is carried out in respect of paths converging on all of the other pivot points distributed (as described in United States Patent Application Ser. No. 934,311, now U.S. Pat. No. 4,178,511) around the body 1.

The above technique, however, suffers from the problem that output signals such as those disposed between points 10 and 12 (the latter being the end of the line) on line 7, between points 13 (the start of corrected line 9) and 10, and corresponding signals relating to other sub-sets are not specifically used, other than in the averaging process. If such signals were merely 'meaned' with corresponding values of used signals, glitches would result. However such signals must be used in order to optimise the usage of radiation dose administered to the patient.

FIG. 2 shows how the above problem can be overcome in accordance with one example of the invention, and it shows on expanded scale the lines 7 and 9 in the vicinity of the point 10, the centre of the overlap zone. It will be appreciated that output signals relating to several beam paths (in this example fourteen beam paths) are derived from each detector in each of the overlap zones such as 6.

In order to use substantially all output signals and yet avoid the production of glitches, the output signals which would otherwise not be specifically used (e.g. those in the regions 13-10 of line 9 and 10-12 of line 7), the invention introduces low frequency corrections and one example of how this can be done will now be described.

It will be appreciated that the object of the invention is to effectively bend the region 13-10 of line 9 until it substantially coincides with line 7 and to bend the region 10-12 of line 7 until it substantially coincides with line 9.

In accordance with one example of the invention, the procedure is as follows:

1. A mean is taken of signals A, B and C on line 7.
2. A mean is taken of signals A', B' and C' on line 9.
3. The difference is added to signal B' and this will cause it to substantially equal the signal B.

For signal C', the procedure is the same as that described above, except that means of signals A to E and A' to E' are differenced and added to C'. For signal D' the means of signals A–G and A'–G' are used; for signal E' the means of signals A–G, H' and I' and A'–G', H and I are used, and so-on in accordance with the following table:

| Signal to be corrected | Signals meaned for correction |
| --- | --- |
| F' | A–G, H'–K' and A'–G', H–K |
| G' | A–G, H'–M' and A'–G', N–M |
| H' | B–G, H'–N' and B'–G', H–N |
| I' | D–G, H'–N' and D'–G', H–N |
| J' | F,G, H'–N' and F',G', H–N |
| K' | H'–N' and H–N |
| L' | J'–N' and J–N |
| M' | L'–N' and L–N |

It will be appreciated that readings A' and N' could use the same corrections as B' and M'. On the other hand, they need not be used as these readings represent only about 7% of the data acquired from the overlap zones and, as such, their non-utilisation is acceptable.

It will be appreciated that the only information added to the "end" signals B' and M' consists of relatively high frequency variations as between adjacent pixels. As the signals approach the point 10, the frequency range of the variations is extended downwards.

The end result of the application of the invention is to substantially, though not completely, equalise signals B and B', C and C', D and D' etc. and these corresponding signals are "meaned" and used for processing. In some circumstances, the overlap zones are not contiguous, so that beam paths in certain zones, between the overlap zones, are viewed by one detector only. If this occurs, the output signals relating to such beam paths can be doubled, prior to processing, to render them compatible with the summed signals derived from the overlap zones.

FIG. 3 shows, in flow diagrammatic form, one arrangement by which the data derived from two detectors, arbitrarily designated the r'th and u'th, can be organised to permit the invention to be implemented. This organisation is, of course, duplicated for all overlap zones in a set of paths. The electrical and electronic circuits necessary for such implementation can be constructed in hard-wired form or may be constituted by a suitably programmed digital computer or may comprise some form of hybrid circuit arrangement.

It is convenient to consider the flow diagram of FIG. 3 in conjunction with the circuit diagram of FIG. 4. In FIG. 4, a CT scanning machine is shown diagrammatically, and it includes an apertured turntable member 14 that can be rotated by conventional means (not shown) around a stationary, apertured support member 16, the relative motion between the two members 14 and 16 being permitted by a large, annular bearing 15 of conventional kind. A patient position 17 is defined within the aperture of the support member 16, and the rotation of member 14 takes place about an axis 18. In operation, a patient to be examined is disposed with a selected cross-sectional slice of his body within the patient position; the axis 18 running longitudinally of the patient's body.

The turntable member 14 carries an X-ray tube 19 which generates a substantially planar, fan-shaped distribution of X-radiation which is projected across the patient position, traversing the aforementioned body slice, to be collected by an array 24 of collimated X-ray detectors. In this example, the X-ray tube has an elongated anode 20 and means such as deflection coils 23 for repetitively deflecting the electron beam 22, generated by a cathode assembly 21, to and fro along the anode at a rate substantially higher than the the rate of rotation of the turntable member 14 about the axis 18. This expedient repeatedly changes the position of the source location, i.e. the region of impingement of the electron beam on the anode, with respect to the detector array, providing benefits which are known and reported, for example in the U.S. Pat. No. 4,178,511 referenced above.

In order to assist in the clear understanding of this invention, FIG. 4 shows only the "glitch" compensating circuits for two detectors, namely the r'th and u'th detectors, of the array 24. It will be appreciated, however, that similar circuits may be provided for each pair of detectors which provide output signals relating to common overlap zones such as 6. Referring again to the drawing, the two detectors feed respective pre-processing circuits 25r and 25u wherein, as is conventional in computerized tomography, the electrical output signals provided by the detectors are amplified, integrated digitised and converted to logarithms. The integration is carried out under the influence of timing pulses generated as a result of the movement of the turntable member 14 around the axis 18 and occurs at regular, brief intervals so that the detector output signals are sampled rapidly and regularly to produce signals relating to the amounts of radiation transmitted across the body slice along many individual, substantially linear beam paths in the sub-sets 4 and 5 respectively.

The signals from pre-processors 25r and 25u are applied to a digital store 26, which can take any convenient form. Address circuits 27 of known kind are arranged to cause the signals derived from the r'th detector, and relating to the overlap zone 6, to be applied in sequence to a summing circuit 28 where they are combined to produce a signal that can conveniently be designated $\Sigma Z_6r$. Likewise, and again under the influence of the address circuits 27, the signals derived from the u'th detector, and relating to the overlap zone 6, are applied in sequence to a summing circuit 29, where they are combined to generate a corresponding signal $\Sigma Z_6u$. The two combined signals, generated by the circuits 28 and 29, are applied to a subtracting circuit 30 wherein the signal $\Sigma Z_6u$ is subtracted from the signal $\Sigma Z_6r$ to produce a signal that can conveniently be designated $\Sigma MOD$. This latter signal $\Sigma MOD$ is added, in a summing circuit 31, to each individual signal, U5, derived from the detector u, in the sub-set 5. This generates modified signals designated U'5 that are stored in a digital store 32. Under the influence of address circuits 33, those modified signals which relate to the overlap zone 6 are applied to a further digital store 34 whence, under the influence of address circuits 35, they can be applied to respective summing circuits 36 and 37.

The summing circuit 36 first receives, from store 34, the modified signals corresponding to the signals A', B' and C' in FIG. 2, i.e. the first three signals derived from the u'th detector in the overlap zone 6, sums them and applies the resultant sum (X') to a subtracting circuit 38. While this has been going on, the signals r6 derived from the r'th detector in relation to the overlap zone 6 have been stored in a digital store 39 and, under the influence of address circuits 40, the signals corresponding to A, B and C in FIG. 2 have been derived from the store 39 and combined in a summing circuit 41. This sum (X) is applied to the subtracting circuit 38 and the arrangement is such that the subtracting circuit 38 forms the difference X–X'; this difference being applied to a summing circuit 44 for combination therein with the signal B' derived from the source 34 under the influence of the address circuits 35.

The arrangement is such that the summing circuit 36 generates, in sequence, the following sums:

| | |
|---|---|
| (a) | A' + B' + C' + D' + E'; |
| (b) | A' + B' + C' + D' + E' + F' + G'; |
| (c) | A' + B' + C' + D' + E' + F' + G' + H + I; |
| (d) | A' + B' + C' + D' + E' + F' + G' + H + I + J + K and |
| (e) | A' + B' + C' + D' + E' + F' + G' + H + I + J + K + L + M |

While the summing circuit 41 generates, in sequence, the following sums:

| | |
|---|---|
| (f) | A + B + C + D + E; |
| (g) | A + B + C + D + E + F + G, |
| (h) | A + B + C + D + E + F + G + H' + I', |
| (i) | A + B + C + D + E + F + G + H' + I' + J' + K', and |
| (j) | A + B + C + D + E + F + G + H' + I' + J' + K' + L' + M'. |

The timing of the operations is such that the sums (a) and (f) are generated simultaneously and are applied to the subtracting circuit 38 which forms the difference (f)−(a) and that difference is supplied to the summing circuit 44 for addition to the signal C'. Likewise, the differences (g)−(b), (h)−(c), (i)−(d) and (j)−(e) are formed sequentially and are added respectively to the signals D', E', F' and G' in circuit 44.

In a similar manner, the signals for combination with the signals H' to N' are generated.

The summing circuit 37 is arranged to form in sequence, the sums:

| | |
|---|---|
| (aa) | B' + C' + D' + E' + F' + G' + H + I + J + K + L + M + N, |
| (bb) | D' + E' + F' + G' + H + I + J + K + L + M + N, |
| (cc) | F' + G' + H + I + J + K + L + M + N, |
| (dd) | H + J + J + K + L + M + N, |
| (ee) | J + K + L + M + N, and |
| (ff) | L + M + N |

A similar summing circuit 42, connected to the digital store 39, is arranged to form the following sums:

| | |
|---|---|
| (gg) | B + C + D + E + F + G + H' + J' + J' + K' + L' + M' + N' |
| (hh) | D + E + F + G + H' + I' + J' + K' + L' + M' + N' |
| (ii) | F + G + H' + I' + J' + K' + L' + M' + N' |
| (jj) | H' + I' + J' + K' + L' + M' + N' |
| (kk) | J' + K' + L' + M' + N' |

-continued (ll)  L' + M' + N'

The timing of the operation is such that the sums (aa) and (gg) are generated simultaneously. These sums are applied to a subtracting circuit 43, which forms the difference (aa)-(gg); that difference being added to the signal H' in a summing circuit 45. Likewise, the differences (bb)-(hh), (cc)-(ii), (dd)-(jj), (ee)-(kk) and (ff)-(ll) are generated in circuit 43 and added, in circuit 45, to the signals I', J', K', L' and M' respectively.

The signals provided by the summing circuits 44 and 45, together with the signals produced by all the other similar circuis, are applied to back-projective CT processing circuits 46 which may, for example, take the form described in U.S. Pat. No. 3,924,129.

It will be appreciated that the action of the circuits 36-38 and 41-43, together with the associated digital stores and addressing circuits, is to generate in sequence individual sums of the first three, five, seven, nine, eleven and thirteen and the last thirteen, eleven, nine, seven, five and three respectively of the signals produced by both the r'th and u'th detectors and relating to the overlaps zone 6 and to subtract corresponding sums derived from the two detectors. These sums are then added to the appropriate and respective ones of signals B' to M' in order to reduce the effects of afterglow on the comparison between the signals produced by different detectors (the r'th and u'th) in respect of a common overlap zone such as 6.

It will be appreciated that the operation of many of the circuits shown in FIG. 4, and in particular the digital stores and their associated addressing circuits is, in known manner, controlled by a master timing circuit (not shown).

In summary, then, it will be appreciated that the invention relates to CT scanners in which zones of overlap occur between sub-sets of beam paths viewed by different detectors. Each overlap zone is used to normalize the output signals derived from the two relevant detectors, but the normalization would be only partially successful, and could result in the occurrence of glitches, in the absence of the invention. In accordance with the invention, the output signals obtained in relation to individual beam paths in the overlap zone are utilised to overcome, or at least reduce, the occurrence of glitches. Signals obtained from the two detectors in relation to a few beam paths at or adjacent the edges of the overlap zone are used to normalise the individual detector outputs for beam paths near the zone edges whereas signals relating to substantially all of the beam paths in the overlap zone are used to normalise individual detector outputs for beam paths at and adjacent the centre of the overlap zone.

I claim:

1. A CT scanner including a source of a substantially planar, divergent spread of penetrating radiation, the radiation propagating across a patient position, detector means sensitive to the radiation and disposed to receive the radiation emergent from said patient position; the detector means including a plurality of detector devices arranged to receive radiation element from said patient position along respective, substantially linear paths and to generate respective electrical output signals indicative of the amounts of radiation so received, scanning means causing said source and said detector means to move angularly around the patient position about a common axis of rotation with the spread of radiation remaining in a plane intersected substantially orthogonally by said axis, and processing means for operating upon output signals generated by said detector means throughout the angular movement to generate a representation of the variation of attenuation of said radiation from place to place over said patient position and in the said plane; the scanning permitting said detector means to generate output signals relating to many sets of paths distributed across the patient position, each set being disposed at a respective attitude to the patient position and consisting of several sub-sets of paths, the radiation propagating along each path of any given sub-set being received by a respective detector device and that propagating along the paths of other sub-sets of the same set being received by different detectors; overlap zones existing between each pair of adjacent sub-sets wherein any two detector devices associated with the paths included in adjacent sub-sets receive radiation along several common paths, the processing means including components operating upon the respective signals generated by the two detector devices in respect of said common paths to generate a respective normalized signal, containing contributions from both detectors, in respect of each of said common paths; each of said normalized signals being generated by comparing output signals relating to different numbers of the paths in the overlap zone for common paths at different positions within the overlap zone, the number of paths involved in the comparison varying, across the overlap zone, from a minimum for common paths at one edge thereof through a maximum in the center thereof to a minimum at the other edge thereof.

2. A CT scanner according to claim 1 including a source having an X-ray emissive anode, means generating an electron beam directed towards said anode and means for repetitively deflecting said beam relative to said anode to repeatedly shift detector devices.

3. A CT scanner according to claim 2 including an array of detectors, of which said first and second detector devices constitute a part, distributed across substantially the full extent of said spread and in the plane thereof.

* * * * *